(12) United States Patent
Guenther et al.

(10) Patent No.: US 6,656,902 B2
(45) Date of Patent: Dec. 2, 2003

(54) CHROMATOGRAPHIC SEPARATION OF ENANTIOMERS OF BICYCLIC LACTAMS

(75) Inventors: Kurt Guenther, Erlensee (DE); Stefan Merget, Rodgau (DE); Karlheinz Drauz, Freigericht (DE); Hans-Peter Krimmer, Dietzenbach (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/741,867

(22) Filed: Dec. 22, 2000

(65) Prior Publication Data

US 2001/0021779 A1 Sep. 13, 2001

(30) Foreign Application Priority Data

Dec. 23, 1999 (DE) .......................... 199 62 543

(51) Int. Cl.⁷ .............................................. B01D 15/08
(52) U.S. Cl. ..................... 510/635; 210/656; 210/659; 435/280; 548/400
(58) Field of Search ................ 210/635, 656, 210/659, 198.2, 502.1; 548/400; 435/280

(56) References Cited

U.S. PATENT DOCUMENTS

| 5,434,299 | A | * | 7/1995 | Negawa et al. | ............ | 216/659 |
|---|---|---|---|---|---|---|
| 5,552,552 | A | * | 9/1996 | Ohkawa et al. | ............ | 546/196 |
| 5,714,479 | A | * | 2/1998 | Ishikawa et al. | ............ | 514/80 |
| 5,733,756 | A | * | 3/1998 | Zeitlin et al. | ............ | 435/122 |
| 5,770,088 | A | * | 6/1998 | Ikeda et al. | ............ | 210/659 |
| 6,277,997 | B1 | * | 8/2001 | Scalone et al. | ............ | 548/226 |
| 6,340,587 | B1 | * | 1/2002 | Dawson et al. | ............ | 435/280 |

FOREIGN PATENT DOCUMENTS

| DE | 197 07 641 | 3/1998 | ............ 210/198.2 |
|---|---|---|---|
| DE | 199 58 497 | 6/2000 | ............ 210/198.2 |
| DE | 199 58 498 | 6/2000 | ............ 210/198.2 |
| EP | 0 424 064 | 4/1991 | ............ 210/198.2 |
| EP | 0 816 339 | 1/1998 | ............ 210/198.2 |
| EP | 0 878 222 | 11/1998 | ............ 210/198.2 |
| WO | WO 98/24741 | 6/1998 | ............ 210/198.2 |
| WO | WO 99/10519 | 3/1999 | ............ 210/198.2 |

OTHER PUBLICATIONS

J. Dingenen and J. N. Kinkel, *Preparative Chromatographic Resolution of Racemates on Chiral Stationary Phases on Laboratory and Production Scales by Closed–Loop Recycling Chromatography*, Journal of Chromatography A, 666 91994) 627–650.

(List continued on next page.)

*Primary Examiner*—Ernest G. Therkorn
(74) *Attorney, Agent, or Firm*—Oblon, Spivak, McClelland, Maier & Neustadt, P.C.

(57) ABSTRACT

A method for separation of enantiomers of a lactam represented by formula (I):

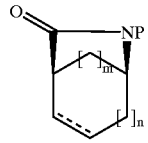

where n and m are each, independently, 0, 1, 2, or 3;

P is H or an N-protecting group; and the dotted line represents an optional double bond, by liquid chromatographing the mixture on a chiral stationary phase, where said stationary phase is derivitized with at least one sugar derivative, with an eluent which comprises acetonitrile.

35 Claims, 4 Drawing Sheets

OTHER PUBLICATIONS

Abstract of Gentilini, J Chromatography 1998, 805(112), 37–44.

Juza et al, *Git Spezial Chromatographie*, 1998; V2, pp. 108.

Schulte et al., *Chemie Ingenieur Technik*, 1966, V.68, pp. 670–683.

H. Uyama, et al., *Peroxidase–Catalyzed Oxidate Polymerization of Cresols to a New Family of Polyphenols*, Bull. Chem. Soc. Jpn., 68, 3209–3214, (1995).

J. Strube, et al., *Comparison of Batch Elution and Continuous Simulated Moving Bed Chromatography*, Organic Process Research & Development, 1998, 2, 305–319.

Marco Mazzoti, et al, "Design of Optimal and Robust Operating Conditions for Chiral Separations Using Simulated Moving Beds", Chiral Europe 1996, pp. 103–112.

\* cited by examiner

CHROMATOGRAPHIC SEPARATION OF ENANTIOMERS OF BICYCLIC LACTAMS

BACKGROUND OF THE INVENTION

1. Field of the Invention

The present invention relates to a method of separating enantiomers of the lactams represented by formula (I):

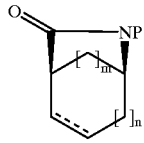

where n and m are each, independently, 0, 1, 2, or 3;

P is H or an N-protecting group; and the dotted line represents an optional double bond.

2. Background of the Invention

The enantiomers of the lactams represented by formula I may be used as the starting materials for the synthesis of a variety of active agents having biological activity, such as carbocyclic nucleoside analogs, which are of interest as drugs in medicine by virtue of their antiviral and chemotherapeutic properties.

Previously, such enantiomers have been prepared preferably from the corresponding racemates by enzymatic racemate resolution (WO 99/10519).

However, the disadvantage of enzymatic separation of enantiomers for a large-scale industrial process is that production must take place in batch operation. Moreover, production and handling of the enzymes used is complex and expensive, and so the overall process is disadvantageous from an economic viewpoint.

Accordingly, there remains a need for methods which overcome these disadvantages.

SUMMARY OF THE INVENTION

It is an object of the present invention to provide a method for the separation of enantiomers of bicyclic lactams represented by formula (I).

It is another object of the present invention to provide a method for the separation of enantiomers of bicyclic lactams represented by formula (I) having lower production costs as compared to other known methods.

In the separation of enantiomers of lactams represented by formula (I):

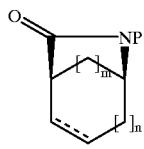

where n and m independently can have values of 0 to 3, P=H or an N-protecting group, by means of an eluent which contains acetonitrile in the method of liquid chromatography on chiral phases containing, i.e., derivitized, with sugar derivatives, it is possible in surprisingly simple but no less advantageous manner to achieve, for the mixtures in question, sufficiently high separation factors, which are necessary for economically advantageous use of this method on the industrial scale and which permit the desired mirror-image isomers of general formula (I) to be produced in resolved form more economically.

Accordingly, the present invention provides a method for separation of enantiomers of a lactam represented by formula (I):

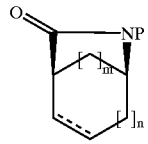

where n and m are each, independently, 0, 1, 2, or 3;

P is H or an N-protecting group; and the dotted line represents an optional double bond, by liquid chromatographing the mixture on a chiral stationary phase, where said stationary phase is derivitized with at least one sugar derivative, with an eluent which comprises acetonitrile.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
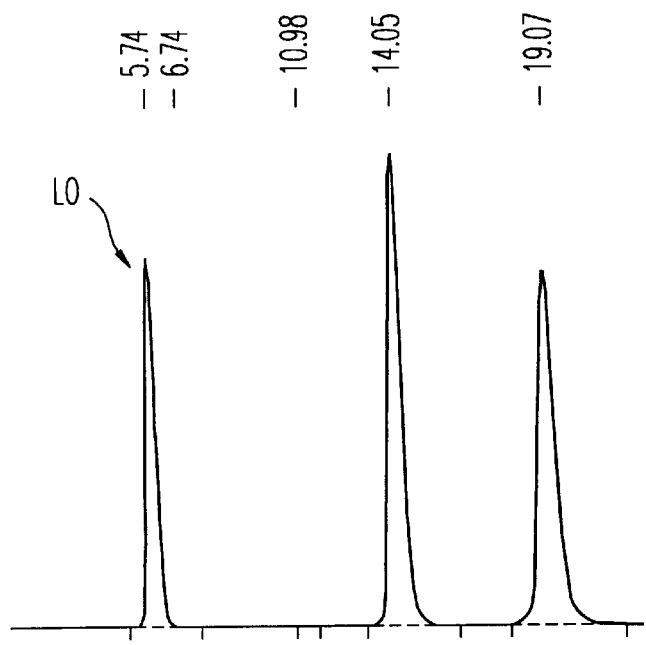
FIG. 1: chromatogram of an HPLC separation of (±)-azabicyclo(2.2.1)-hept-5-en-3-one on a Chiralpak® AS 250×4.6 mm column using acetonitrile as the eluant.

In a preferred embodiment, the inventive method is used to resolve the racemate of (±)-azabicyclo(2.2.1)-hept-5-en-3-one into the corresponding enantiomers.

As discussed above, the resolution of the enantiomers in question on the industrial scale can be achieved by the method of liquid chromatography. The general principle of liquid chromatography is well-known to those of ordinary skill in the art. For example, separations with so-called "pancake columns" in the batch chromatography method are suitable. Particularly preferred, however, is the use of quasi-continuous cyclic liquid chromatography, possibly with "recycling" and "peak shaving" (J. Chromatogr. 1994, 666, 627–650), or the method of continuous SMB chromatography (Mazzotti et al., Chiral Europe 1996, 103 if.; Strube et al., Organic Process Research & Development 1998, 2, 305–319; Juza et al., GIT Spezial Chromatographie 1998, 2, 108 ff.; European Patent 0878222; Schulte et al., Chemie Ingenieur, Technik 1966, 68, 670–683).

The stationary phase used in the method of the present invention is derivitized with at least one sugar derivative. Preferred sugar derivatives include those based on amylose or cellulose. Several derivatives modified in this way are known (see Bull. Chem. Soc. Jpn. 1995, 68, 3209–3307). Esters and carbamates of these materials in particular are suitable. For this purpose the sugar derivatives can be used in native form or absorbed on a support material. Silica gel is preferred as a suitable support material. It has been found particularly advantageous to use a material containing sugar derivatives or microcrystalline cellulose esters absorbed on silica gel. Extremely preferred is the use of amylose-derivatized silica gel columns as the stationary phase (such as Chiralpak AS® from Daicel Co.).

The moving phase used in the present invention, i.e., the eluant, preferably contains acetonitrile. To improve the separation capabilities, however, acetonitrile maybe mixed with other solvents which are suitable for HPLC. In a preferred embodiment, however, acetonitrile is the main component of the moving phase mixture. Methanol has proved to be a preferred solvent in such mixtures. Especially preferred is the embodiment in which acetonitrile and methanol are present as main components in the moving phase mixture. Thus, the eluent preferably contains at least 50% by volume of acetonitrile. Alternatively the eluant may contain at least 70%, 80%, or 90% by volume of acetonitrile.

Generally, the pressure or temperature used for the separation may vary over a wide range. The parameters should be matched to one another such that optimal separation capacity is achieved at the highest possible flowrates. Usually, the pressure to be used ranges from 0.3 to 2.0 MPa, preferably from 0.5 to 0.7 MPa, and the temperature from 20 to 40° C., preferably 22 to 28° C.

The subject matter of the invention also includes the use of the mirror-image isomers of the lactam of formula (I) synthesized according to the invention for synthesis of active agents having biological activity. Such transformations are well-known to those of ordinary skill in the art of organic synthesis. Preferably, the active agent produced from the enantiomer is a carbocyclic nucleoside analog.

The present inventive separation method takes place in very robust manner as compared to enzymatic methods. The materials used have long shelf lives and the method also permits continuous synthesis of the enantiomers, which is extremely advantageous for an industrial process.

A chromatographic separation of the enantiomers of these substances as described herein has never yet been mentioned in the literature. The choice of column material and moving phase from the several thousands of possible combinations makes possible the simple and nevertheless very successful separation of the enantiomers.

Within the scope of the invention the term protective group is understood as a moiety selected from the group comprising formyl, acetyl, propionyl, methoxycarbonyl, ethoxycarbonyl, tert-butoxycarbonyl, Z, Fmoc, or benzyl.

The dashed line in formula (I) means that a double bond can be optionally present the two carbon atoms.

As used herein, the term "liquid chromatography" refers to low pressure liquid chromatography (LPLC), medium pressure liquid chromatography (MPLC) or high pressure liquid chromatography (HPLC).

The separation factor is calculated as follows:

Separation factor=$(T_0-T_{D/(T0}-T_2)$ $T_0$=1,3,5-tert-butylbenzene

Preferably, the separation factor achieved with the method of the present invention is at least 1.1. Preferably, the separation factor is higher than this value, such as at least 1.2, 1.3, 1.4, or 1.6, or even higher.

In another embodiment of the present invention, the enantiomers isolated from the stationary phase have an enantiomer excess value (ee) of at least 50%. Preferably, the ee is at least 80%, more preferably at least 95%, and most preferably at least 98%. The ee may be 99%, 99.5%, or even higher.

EXAMPLES

Having generally described this invention, a further understanding can be obtained by reference to certain specific examples which are provided herein for purposes of illustration only and are not intended to be limiting unless otherwise specified.

HPLC Separation of (±)-azabicyclo(2.2.1)-hept-5-en-3-one on Chiral Columns

Figure 2:
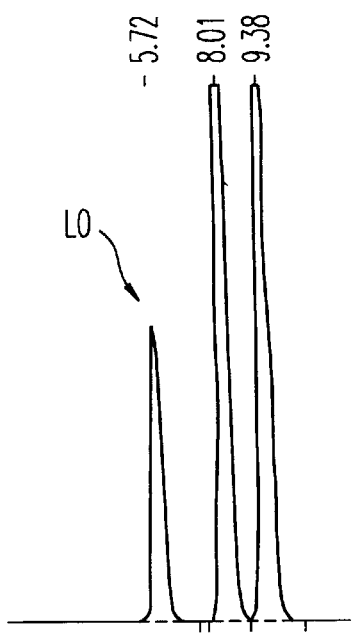
FIG. 2: chromatogram of an HPLC separation of (±)-azabicyclo(2.2.1)-hept-5-en-3-one on a Chiralpak® AS 250×4.6 mm column using acetonitrile/methanol (80:20 (v/v)) as the eluant.
Figure 3:
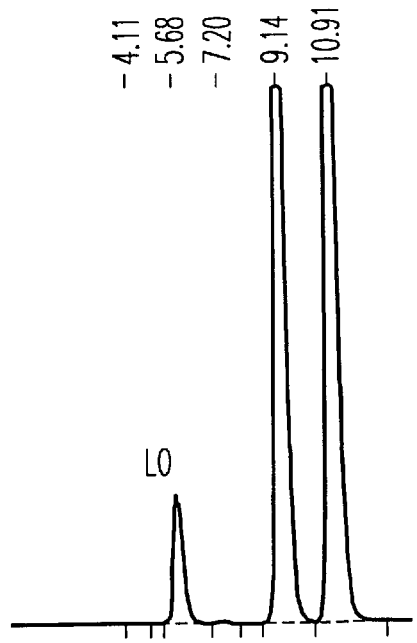
FIG. 3: chromatogram of an HPLC separation of (±)-azabicyclo(2.2.1)-hept-5-en-3-one on a Chiralpak® AS 250×4.6 mm column using acetonitrile/methanol (80:20 (v/v)) as the eluant.
Figure 4:
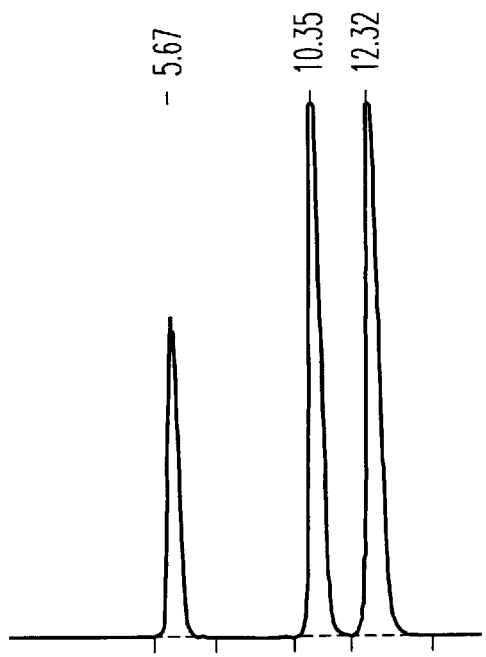
FIG. 4: chromatogram of an HPLC separation of (±)-azabicyclo(2.2.1)-hept-5-en-3-one one on a Chiralpak® AS 250×4.6 mm column using acetonitrile/2-propanol as the eluant.
Figure 5:
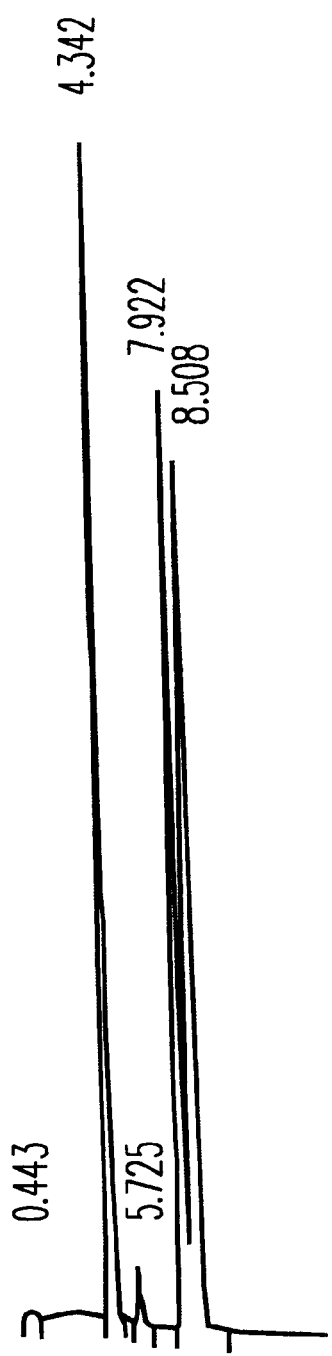
FIG. 5: chromatogram of an HPLC separation of (±)-azabicyclo(2.2.1)-hept-5-en-3-one on a Chiralpak® AS 250×4.6 mm column using acetonitrile as the eluant.
Figure 6:
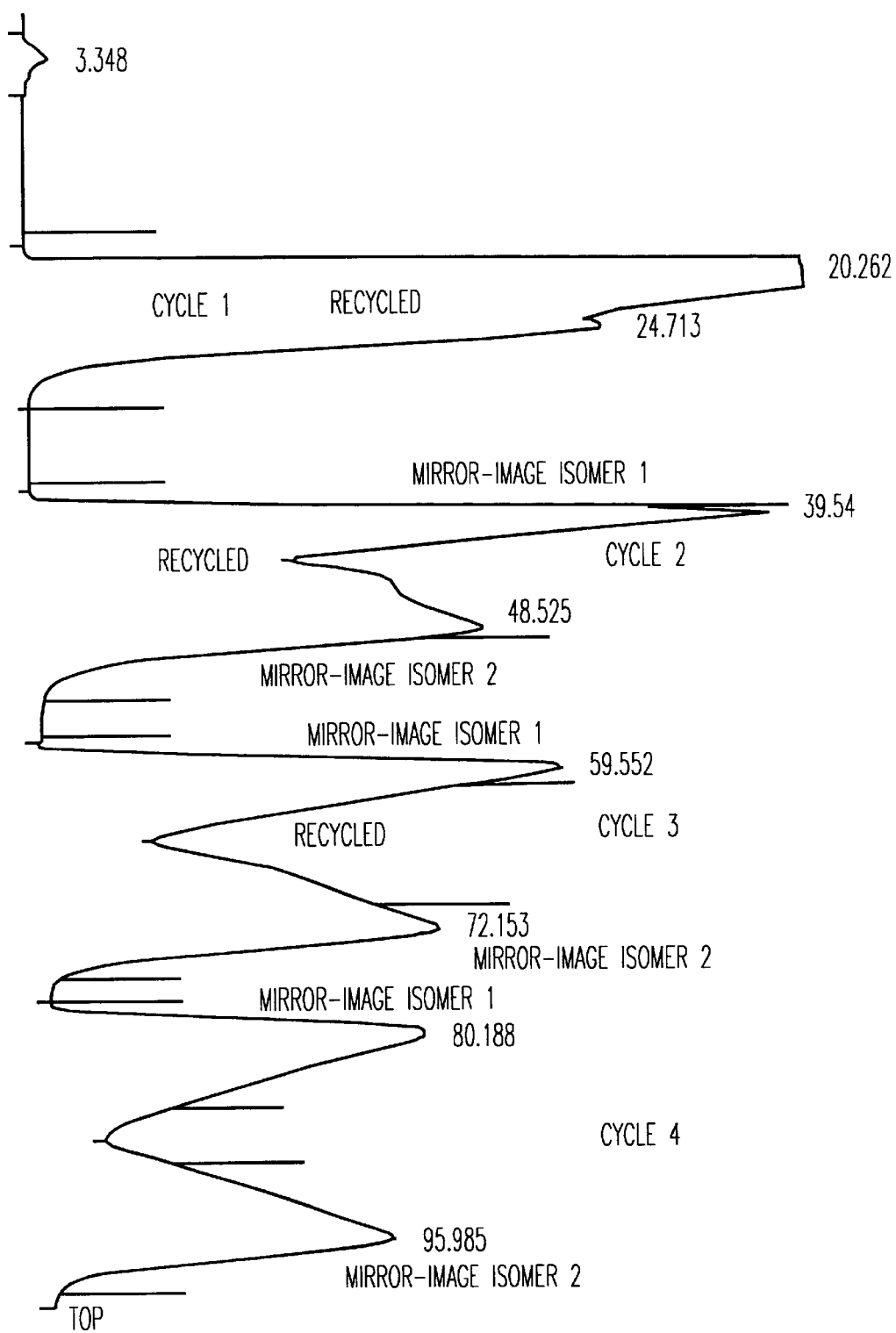
FIG. 6: chromatogram of a quasi-continuous cyclic HPLC separation of (±)-azabicyclo(2.2.1)-hept-5-en-3-one on a Chiralpak® AS 250×4.6 mm column using acetonitrile as the eluant.

Sample: 10 mg each of (±)-azabicyclo(2.2.1)-hept-5-en-3-one and 1,3,5-tri-tert-butylbenzene (Fluka) as $T_0$ markers are weighed into a 10 ml volumetric flask and made up to the mark with the respective eluent. 20 µl of this solution is injected.

a) Column: Chiralpak® AS 250×4.6 mm (Daicel)
Eluent: acetonitrile
Flowrate: 0.6 ml/min
Temperature: 25° C.
Wavelength: 230 nm
Result: see FIG. 1
Separation factor α=1.6 b) Column: Chiralpak® AS 250×4.6 mm (Daicel)
Eluent: acetonitrile/methanol, 80:20 (v/v)
Flowrate: 0.6 m/min
Temperature: 25° C.
Wavelength: 230 nm
Result: see FIG. 2
Separation factor α=1.6 c) Column: Chiralpak® AS 250×4.6 mm (Daicel)
Eluent: acetonitrile/ethanol, 80:20 (v/v)
Flowrate: 0.6 ml/min
Temperature: 25° C.
Wavelength: 230 nm
Result: see FIG. 3
Separation factor α=1.51 d) Column: Chiralpak® AS 250×4.6 mm (Daicel)
Eluent: acetonitrile/2-propanol, 80:20 (v/v)
Flowrate: 0.6 ml/min
Temperature: 25° C.
Wavelength: 230 nm
Result: see FIG. 4
Separation factor α=1.42 e) Column: Chiralpak® AD 250×4.6 mm (Daicel)
Eluent: acetonitrile
Flowrate: 0.6 ml/min
Temperature: 25° C.
Wavelength: 230 nm Result: see FIG. 5
Separation factor 1.17
Quasi-continuous cyclic versions
Column: Chiralpak® AD 250×40 mm (Daicel)
Column packing: suspend 220 g of support material (20 μm) in 1400 ml of acetonitrile and transfer into the filling tube, cover with acetonitrile up to the top rim, firmly seal the filling tube and compact the column material at 150 bar.
Eluent: acetonitrile
Flowrate: 60 ml/min
Pressure: about 60 to 80 bar
Temperature: 22° C.
Wavelength: 230 nm
Sample preparation: 150 mg of (±)-azabicyclo(2.2.1)-hept-5-en-3-one is dissolved in 15 ml of eluent and filtered through a membrane filter. The total volume of the clear filtrate is placed on the column. About 1.5 g of racemate in total is chromatographed.
Fractionation: Resolution of the racemate is achieved in six cycles. Cycle 1 is completely recycled. Starting from cycle 2 the fractionation of the individual mirror-image isomers takes place at the points marked on the chromatogram (FIG. 6).
Working up: The united fractions of the individual cycles are concentrated to dryness in a rotary evaporator at about 250 to 350 mbar and a water-bath temperature of about 40 to 45° C.
Result: At a yield of 85%, the (±)-enantiomer is obtained with an enantiomeric excess value of >97.5% and the (−)-enantiomer with an enantiomeric excess value of 98%.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 199 62 543.3, filed on Dec. 23, 1999, and incorporated herein by reference in its entirety.

What is claimed is:

1. A method of separating the enantiomers of a mixture of the enantiomers of a lactam represented by formula (I):

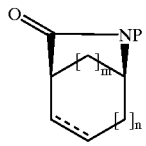

wherein
n and m are each, independently, 0, 1, 2, or 3;
P is H or an N-protecting group; and
the dotted line represents an optional double bond,
comprising:
separating said enantiomers to an enantiomeric excess value of at least 80% by liquid chromatographing said mixture on a chiral stationary phase, wherein said stationary phase is derivitized with at least one sugar derivative, with an eluent which comprises acetonitrile.

2. The method of claim 1, wherein said mixture contains (±)-azabicyclo(2.2.1)-hept-5-en-3-one.

3. The method of claim 1, wherein said liquid chromatographing is cyclic or SMB chromatography.

4. The method of claim 1, wherein said at least one sugar derivative is an ester or a carbamate of an amylose or a cellulose.

5. The method of claim 1, wherein said stationary phase comprises a material which contains sugar derivatives or microcrystalline cellulose esters absorbed on silica gel.

6. The method of claim 1, wherein said stationary phase is an amylose-derivatized silica gel column.

7. The method of claim 1, wherein the main component of said eluant is acetonitrile.

8. The method of claim 1, wherein said eluant further comprises methanol.

9. The method of claim 1, wherein said eluant contains at least 50% by volume of acetonitrile.

10. The method of claim 1, wherein said eluant contains at least 75% by volume of acetonitrile.

11. The method of claim 1, wherein said eluant contains at least 80% by volume of acetonitrile.

12. The method of claim 1, wherein said eluant contains at least 90% by volume of acetonitrile.

13. The method of claim 1, wherein said eluant consists of acetonitrile.

14. The method of claim 1, wherein said eluant contains acetonitrile or acetonitrile and methanol as the main components.

15. The method of claim 1, wherein said liquid chromatographing is performed at a pressure of 0.3 to 2.0 MPa.

16. The method of claim 1, wherein said liquid chromatographing is performed at a pressure 0.5 to 0.7 MPa.

17. The method of claim 1, wherein said liquid chromatographing is performed at a temperature of 20 to 40° C.

18. The method of claim 1, wherein said liquid chromatographing is performed at a temperature of 22 to 28° C.

19. The method of claim 1, wherein P is H.

20. The method of claim 1, wherein P is an N-protecting group selected from the group consisting of formyl, acetyl, propionyl, methoxycarbonyl, ethoxycarbonyl, tert-butoxycarbonyl, Z, Fmoc, and benzyl.

21. The method of claim 1, wherein the separation factor achieved with said liquid chromatographing is at least 1.1.

22. The method of claim 1, wherein said enantiomeric excess value is at least 95%.

23. The method of claim 1, wherein said enantiomeric excess value is at least 97.5%.

24. The method of claim 1, wherein said enantiomeric excess value is at least 98%.

25. The method of claim 1, wherein said enantiomeric excess value is at least 99%.

26. The method of claim 1, wherein said enantiomeric excess value is at least 99.5%.

27. The method of claim 1, wherein said liquid chromatographing achieves a separation factor of at least 1.2.

28. The method of claim 1, wherein said liquid chromatographing achieves a separation factor of at least 1.3.

29. The method of claim 1, wherein said liquid chromatographing achieves a separation factor of at least 1.4.

30. The method of claim 1, wherein said liquid chromatographing achieves a separation factor of at least 1.6.

31. The method of claim 1, which is carried out on an industrial scale.

32. The method of claim 1, wherein said liquid chromatographing is quasi-continuous cyclic liquid chromatography.

33. The method of claim 1, further comprising isolating at least one enantiomer from said stationary phase.

34. A method of synthesizing an active agent having biological activity, comprising:
isolating said at least one enantiomer according to the method of claim 33, and then converting said enantiomer into said active agent.

35. The method of claim 34, wherein said active agent is a carbocyclic nucleoside analog.

* * * * *